(12) United States Patent
Badejo et al.

(10) Patent No.: US 7,932,305 B2
(45) Date of Patent: Apr. 26, 2011

(54) VISCOUS α-CYANOACRYLATE COMPOSITIONS

(75) Inventors: Ibraheem T. Badejo, Raleigh, NC (US); Teresa Marie Warren, Raleigh, NC (US); Brian McCrum, Raleigh, NC (US)

(73) Assignee: Ethicon, Inc., Somerville, NJ (US)

( * ) Notice: Subject to any disclaimer, the term of this patent is extended or adjusted under 35 U.S.C. 154(b) by 38 days.

(21) Appl. No.: 12/147,582

(22) Filed: Jun. 27, 2008

(65) Prior Publication Data

US 2009/0326095 A1    Dec. 31, 2009

(51) Int. Cl.
*A61K 47/32* (2006.01)
*C08F 118/02* (2006.01)

(52) U.S. Cl. .................. 523/118; 526/319
(58) Field of Classification Search .......... 523/113, 523/114, 115, 116, 118, 20; 526/298
See application file for complete search history.

(56) References Cited

U.S. PATENT DOCUMENTS

| | | | |
|---|---|---|---|
| 2,721,858 A | 10/1955 | Overhults | |
| 3,254,111 A | 5/1966 | Hawkias | |
| 3,697,618 A * | 10/1972 | Grunewalder et al. | 526/271 |
| 3,940,362 A * | 2/1976 | Overhults | 523/116 |
| 3,995,641 A | 12/1976 | Kronenthal | |
| 4,038,345 A * | 7/1977 | O'Sullivan et al. | 525/284 |
| 4,313,865 A | 2/1982 | Teramoto et al. | |
| 4,364,876 A | 12/1982 | Kimura et al. | |
| 4,560,723 A | 12/1985 | Millet et al. | |
| 4,720,513 A | 1/1988 | Kameyama et al. | |
| 5,328,687 A | 7/1994 | Leung et al. | |
| 5,575,997 A | 11/1996 | Leung et al. | |
| 5,582,834 A | 12/1996 | Leung et al. | |
| 5,624,669 A | 4/1997 | Leung et al. | |
| 5,928,611 A | 7/1999 | Leung | |
| 6,010,714 A | 1/2000 | Leung et al. | |
| 6,310,166 B1 * | 10/2001 | Hickey et al. | 526/348.2 |
| 6,433,096 B1 | 8/2002 | Hickey et al. | |
| 6,579,469 B1 | 6/2003 | Nicholson et al. | |
| 6,579,916 B1 * | 6/2003 | Askill et al. | 522/152 |
| 6,620,846 B1 * | 9/2003 | Jonn et al. | 514/519 |
| 6,802,416 B1 | 10/2004 | D'Alessio et al. | |
| 7,008,635 B1 * | 3/2006 | Coury et al. | 424/426 |
| 7,484,564 B2 * | 2/2009 | Welton et al. | 166/276 |
| 7,534,907 B2 * | 5/2009 | Liu | 558/442 |
| 2002/0037310 A1 * | 3/2002 | Jonn et al. | 424/448 |
| 2003/0039781 A1 | 2/2003 | D'Alessio et al. | |
| 2005/0109976 A1 * | 5/2005 | Fuchs et al. | 252/62.54 |
| 2005/0165128 A1 * | 7/2005 | Cohn et al. | 523/105 |
| 2006/0013853 A1 * | 1/2006 | Richard | 424/423 |

FOREIGN PATENT DOCUMENTS

EP        0 617 973 A1    10/1994
WO    WO 01/12243 A1     2/2001

OTHER PUBLICATIONS

Rehberg, C.E. et al., "Polymerizable Esters of Lactic Acid. Alpha-Carbalkoxyethyl Acrylates and Methacrylates", Journal of the American Chemical Society, vol. 67, (1945), pp. 208-210.

Licea-Claverie, A. et al., "The use of hydrophobic spacers in the development of new temperature—and pH-sensitive polymers", Macromolecular Symposia, vol. 207, (2004), pp. 193-215.

* cited by examiner

*Primary Examiner* — Mark Eashoo
*Assistant Examiner* — Peter F Godenschwager

(57) ABSTRACT

A polymerizable adhesive composition comprises at least one α-cyanoacrylate monomer and at least one absorbable viscosity modifying agent. The absorbable viscosity modifying agent has repeated units of the following structure:

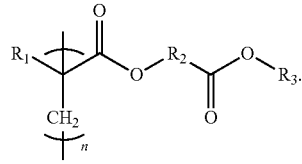

$R_1$ is a methyl group or a hydrogen. $R_2$ is a straight, branched or cyclic alkyl group having from 1 to 6 carbon atoms. $R_3$ is a straight, branched or cyclic alkyl group having from 1 to 12 carbon atoms, and n is 2 or more.

19 Claims, No Drawings

VISCOUS α-CYANOACRYLATE COMPOSITIONS

FIELD OF THE INVENTION

The invention relates to absorbable viscosity modifying agents for adhesives or sealants, and more particularly to cyanoacrylate monomer compositions. This invention further relates to the use of such viscosity modifying agents and cyanoacrylate monomers as tissue adhesives/sealant compositions in surgical, medical and industrial applications, and to the production thereof.

BACKGROUND

Monomer and polymer adhesives/sealants are used in both industrial (including household) and medical/surgical applications. Included among these adhesives or sealants are cyanoacrylates monomers and polymers resulting therefrom. Since the discovery of the adhesive/sealant properties of such monomers and polymers, they have found wide use due to the speed with which they cure, the strength of the resulting bond formed, and their relative ease of use. These characteristics have made α-cyanoacrylate compositions the primary choice for numerous adhesive applications such as bonding plastics, rubbers, glass, metals, wood, and, more recently, medical, biological or living tissues.

Medical and surgical applications of α-cyanoacrylate compositions include their use as alternates or adjuncts to surgical sutures, meshes and staples or other medical devices in wound closure, as well as for covering and protecting surface wounds such as lacerations, abrasions, burns, stomatitis, sores, and other surface wounds. When an α-cyanoacrylate composition is applied, it is usually applied in its monomeric form, and the resultant polymer creates the desired adhesive bond or sealant strength.

At standard temperatures, the monomeric α-cyanoacrylate may run when applied to surfaces. As a result, the α-cyanoacrylate adhesive may spread into a wound or along a surface to which it has been applied to areas that do not require an adhesive and that may be adversely affected by an adhesive. Therefore, it is desirable to control the viscosity of the monomeric α-cyanoacrylate composition in order to prevent escape of the adhesive from the area of application. In order to reduce run-off or achieve a suitably viscous adhesive, a thickening or viscosity modifying agent may be added to a monomeric α-cyanoacrylate composition.

Polymerizable α-cyanoacrylate monomers and compositions comprising such monomers are disclosed in U.S. Pat. No. 5,328,687. Further, the use of polymers as thickening agents for α-cyanoacrylate monomers and compositions is disclosed in U.S. Pat. No. 6,433,096. Each of the above documents is incorporated by reference herein in its entirety.

For some medical applications, an absorbable thickening or viscosity modifying agent provides benefits over a non-absorbable thickening or viscosity modifying agent. For example, it is desirable to have a monomer-based internal adhesive or sealant composition that polymerizes in vivo, where the monomer, the composition thereof, and the resultant polymer are biocompatible. It is also desirable to use an adhesive or sealant composition that fills internal cavities and voids, penetrating and conforming to the interstices and pores of the tissue, prior to curing or setting. Finally, it is desirable that the resultant polymer also be biodegradable, so that the degradation products are completely eliminated from the human body as waste products.

Therefore, there is a need for an absorbable and biocompatible viscosity modifying agent for α-cyanoacrylate compositions that exhibits controlled viscosity and absorbability sufficient for medical applications and produces a polymer adhesive/sealant that may also be biodegradable.

While it is desirable to have an adhesive that is biodegradable, achieving such biodegradability should not adversely affect other desirable properties of the adhesive, e.g., stability. In order for an adhesive to be a commercially viable product, it is preferred that the monomeric form of the adhesive have a shelf life of at least one year at standard, non-refrigerated, temperatures.

Therefore, there is a need for an α-cyanoacrylate adhesive composition that is absorbable and biocompatible and also stable enough to be commercially viable.

SUMMARY

The present invention relates to a monomer composition comprising at least one α-cyanoacrylate monomer and at least one absorbable viscosity modifying agent, which monomer polymerizes to form an adhesive or sealant possessing controlled viscosity and is minimally toxic to non-toxic.

The absorbable viscosity modifying agent has repeated units of the following structure:

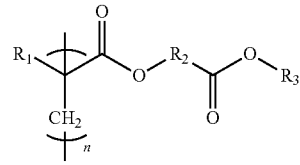

wherein $R_1$ is a methyl group or a hydrogen, $R_2$ is a straight, branched or cyclic alkyl group having from 1 to 6 carbon atoms, $R_3$ is a straight, branched or cyclic alkyl group having from 1 to 12 carbon atoms, and n is 2 or more.

The present invention includes many aspects and features.

The at least one absorbable viscosity modifying agent may be selected from the group consisting of a polymer of 2-methoxy-2-oxoethyl acrylate, 2-ethoxy-2-oxoethyl acrylate, 2-oxo-2-propoxyethyl acrylate, 2-butoxy-2-oxoethyl acrylate, 2-methoxy-2-oxoethyl methacrylate, 2-ethoxy-2-oxoethyl methacrylate, 2-oxo-2-propoxyethyl methacrylate, 2-butoxy-2-oxoethyl methacrylate, 1-methoxy-1-oxopropan-2-yl acrylate, 1-ethoxy-1-oxopropan-2-yl acrylate, 1-oxo-1-propoxypropan-2-yl acrylate, 1-butoxy-1-oxopropan-2-yl acrylate, 1-methoxy-1-oxopropan-2-yl methacrylate, 1-ethoxy-1-oxopropan-2-yl methacrylate, 1-oxo-1-propoxypropan-2-yl methacrylate, 1-butoxy-1-oxopropan-2-yl methacrylate, and mixtures thereof.

DETAILED DESCRIPTION

For the purposes of this invention, the term "absorbable" or variations thereof means capable of being absorbed, degraded or biodegraded, either fully or partially, by animal (including human) tissue after application of the adhesive or sealant. Also, the term "substantially absorbed" means at least 90% absorbed. The term "non-absorbable" or variations thereof means completely or substantially incapable of being absorbed, either fully or partially, by animal tissue after application of the adhesive or sealant.

The term "effective amount" is an amount sufficient to provide desired properties to the adhesive compositions. The effective amount may be affected by α-cyanoacrylate monomers, viscosity modifying agents, stabilizers, initiators or other ingredients used to form the adhesive composition.

The term "stability" or "stabilized" as used herein may be determined by measuring the viscosity of the α-cyanoacrylate composition over a period of time. Premature polymerization of the α-cyanoacrylate composition results in an increase in viscosity over time; therefore, viscosity of a composition may be used to determine composition stability.

The adhesive/sealant compositions of the present invention comprise a new member of carbalkoxyalkyl acrylate or carbalkoxyalkyl methacrylate as an absorbable viscosity modifying agent. The new members of carbalkoxyalkyl acrylate or carbalkoxyalkyl methacrylate have repeated units of the following structure;

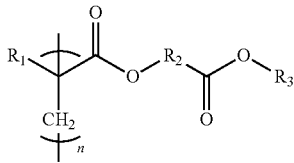

wherein $R_1$ is a methyl group or a hydrogen, $R_2$ is a straight, branched or cyclic alkyl group having from 1 to 6 carbon atoms, $R_3$ is a straight, branched or cyclic alkyl group having from 1 to 12 carbon atoms, and n is 2 or more.

An exemplary new member of carbalkoxyalkyl methacrylate is 1-butoxy-1-oxopropan-2-yl methacrylate or butyl lactoyl methacrylate (BLMA). The BLMA monomer and polymer are not available commercially, and may be synthesized as described herein in Example 1. The BLMA polymer is particularly useful as a viscosity modifying agent because it is compatible with α-cyanoacrylate monomers. Also, the BLMA polymer is preferred for certain medical applications as a viscosity modifying agent because is absorbable. The addition of an absorbable BLMA polymer to an absorbable adhesive composition provides controlled viscosity and maintains the absorbability of the adhesive composition. Thus the resulting adhesive polymer formed thereof may be absorbable or substantially absorbed by living tissues. The BLMA polymer has repeated units of

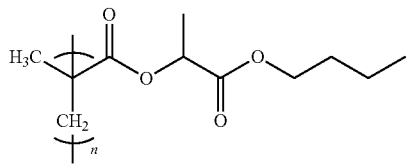

In embodiments, the BLMA polymer has a high molecular weight, preferably at least 250,000 Daltons and more preferably at least 500,000 Daltons. The BLMA polymer is soluble in an α-cyanoacrylate monomer composition at room temperature (i.e., 20-25° C.). Thus it may be added to the monomer composition without excessive heating of the composition and may remain uniformly combined in the composition. The BLMA polymer may be used in α-cyanoacrylate adhesive compositions in an effective amount, for example, from about 1.0% to about 15.0% by weight of the adhesive composition. The BLMA polymer may be used in an amount from about 2.0% to about 8.0% by weight, preferably, from about 5.0% to about 7.5% by weight of the adhesive composition.

The effective amount of the BLMA polymer in the adhesive composition may provide a viscosity of about 20 to about 1,000 centipoise, preferably about 50 to about 800 centipoise, as measured with a Brookfield Viscometer at 25° C.

Other suitable members of carbalkoxyalkyl acrylate or carbalkoxyalkyl methacrylate, new or known include, but are not limited to, 2-methoxy-2-oxoethyl acrylate, 2-ethoxy-2-oxoethyl acrylate, 2-oxo-2-propoxyethyl acrylate, 2-butoxy-2-oxoethyl acrylate, 2-methoxy-2-oxoethyl methacrylate, 2-ethoxy-2-oxoethyl methacrylate, 2-oxo-2-propoxyethyl methacrylate, 2-butoxy-2-oxoethyl methacrylate, 1-methoxy-1-oxopropan-2-yl acrylate, 1-ethoxy-1-oxopropan-2-yl acrylate, 1-oxo-1-propoxypropan-2-yl acrylate, 1-butoxy-1-oxopropan-2-yl acrylate, 1-methoxy-1-oxopropan-2-yl methacrylate, 1-ethoxy-1-oxopropan-2-yl methacrylate, and 1-oxo-1-propoxypropan-2-yl methacrylate. The polymers of above listed members of carbalkoxyalkyl acrylate or carbalkoxyalkyl methacrylate, either alone or in combination, may be used as viscosity modifying agents herein.

The sealant/adhesive composition of the present invention also comprises at least one polymerizable α-cyanoacrylate monomer. Preferably, the adhesive composition comprises one or more polymerizable α-cyanoacrylate monomers and may include combinations or mixtures of α-cyanoacrylate monomers.

The α-cyanoacrylates monomers are known in the art and have the formula (I)

wherein $R^2$ is hydrogen and $R^3$ is a hydrocarbyl or substituted hydrocarbyl group; a group having the formula —$R^4$—O—$R^5$—O—$R^6$, wherein $R^4$ is a 1,2-alkylene group having 2-4 carbon atoms, $R^5$ is an alkylene group having 1-4 carbon atoms, and $R^6$ is an alkyl group having 1-6 carbon atoms; or a group having the formula

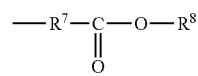

wherein $R^7$ is

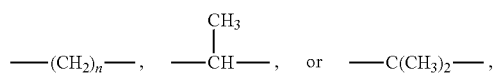

wherein n is 1-10, preferably 1-5 carbon atoms, and $R^8$ is an organic moiety. The organic moiety $R^8$ may be substituted or unsubstituted and may be straight chain, branched or cyclic, saturated, unsaturated or aromatic. Preferred organic radicals are alkyl, alkenyl, and alkynyl moieties having from 1 to about 8 carbon atoms, and halo-substituted derivatives thereof. Particularly preferred are alkyl moieties of 4 to 6 carbon atoms.

In the α-cyanoacrylate monomer of formula (I), $R^3$ may be an alkyl group having 1-10 carbon atoms or a group having the formula -AOR$^9$, wherein A is a divalent straight or branched chain alkylene or oxyalkylene moiety having 2-8 carbon atoms, and $R^9$ is a straight or branched alkyl moiety having 1-8 carbon atoms. Examples of groups represented by the formula -AOR$^9$ include 1-methoxy-2-propyl, 2-butoxy ethyl, isopropoxy ethyl, 2-methoxy ethyl, and 2-ethoxy ethyl.

The α-cyanoacrylates of formula (I) can be prepared according to methods known in the art. For example, α-cyanoacrylates can be prepared by reacting an alkyl cyanoacetate with formaldehyde in a nonaqueous organic solvent and in the presence of a basic catalyst, followed by pyrolysis of the anhydrous intermediate polymer in the presence of a polymerization inhibitor as disclosed in U.S. Pat. Nos. 2,721,858 and 3,254,111. The α-cyanoacrylates of formula (I) wherein R$^1$ is a group having the formula R$^4$—O—R$^5$—O—R$^6$ can be prepared according to the method disclosed in U.S. Pat. No. 4,364,876, and the α-cyanoacrylates of formula (I) wherein R$^3$ is a group having the formula

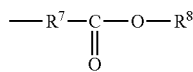

can be prepared according to the method described in U.S. Pat. No. 3,995,641. Each of the above listed patents is hereby incorporated by reference in its entirety.

Suitable α-cyanoacrylate monomers may be used, alone or in combination, and may include, but not be limited to, 2-octyl cyanoacrylate; dodecyl cyanoacrylate; 2-ethylhexyl cyanoacrylate; butyl cyanoacrylate such asn-butyl cyanoacrylate; ethyl cyanoacrylate; methyl cyanoacrylate; methoxyethyl cyanoacrylate; 2-ethoxyethyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. In embodiments, the monomers may be ethyl, n-butyl, or 2-octyl α-cyanoacrylate.

The α-cyanoacrylate monomers which may be used in the adhesive/sealant compositions may include alkyl ester cyanoacrylates. The alkyl ester cyanoacrylate monomers may have the formula:

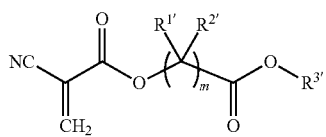

wherein R$^{1'}$ and R$^{2'}$ are, independently, H, a straight, branched or cyclic alkyl, or are combined together in a cyclic alkyl group, R$^{3'}$ is a straight, branched or cyclic alkyl group, and m is 1-8. Preferably, R$^{1'}$ is H or a C$_1$, C$_2$ or C$_3$ alkyl group, such as methyl or ethyl; R$^2$ is H or a C$_1$, C$_2$ or C$_3$ alkyl group, such as methyl or ethyl; R$^{3'}$ is a C$_1$-C$_{16}$ alkyl group, more preferably a C$_1$-C$_{10}$ alkyl group, such as methyl, ethyl, propyl, isopropyl, butyl, isobutyl, pentyl, hexyl, heptyl, octyl, nonyl or decyl, and even more preferably a C$_2$, C$_3$ or C$_4$ alkyl group, and m is preferably 1-4.

Examples of alkyl ester cyanoacrylates include, but are not limited to, butyl lactoyl cyanoacrylate (BLCA), butyl glycoloyl cyanoacrylate (BGCA), isopropyl glycoloyl cyanoacrylate (IPGCA), ethyl lactcyl cyanoacrylate (ELCA), and ethyl glycoloyl cyanoacrylate (EGCA) and combinations thereof. BLCA may be represented by the formula above, wherein R$^{1'}$ is H, R$^{2'}$ is methyl and R$^{3'}$ is butyl. BGCA may be represented by the formula above, wherein R$^{1'}$ is H, R$^{2'}$ is H and R$^3$ is butyl. IPGCA may be represented by the formula above, wherein R$^{1'}$ is H, R$^{2'}$ is H and R$^{3'}$ is isopropyl. ELCA may be represented by the formula above, wherein R$^{1'}$ is H, R$^{2'}$ is methyl and R$^{3'}$ is ethyl. EGCA may be represented by the formula above, wherein R$^{1'}$ is H, R$^{2'}$ is H and R$^{3'}$ is ethyl.

Other examples of alkyl ester cyanoacrylates include 3-(2-Cyano-acryloyloxybutyric acid ethyl ester (Et-β-HBT-CA), 3-(2-cyano-acryloyloxy)-hexanoic acid ethyl ester (Et-β-CPL-CA), alkyl alpha-cyanoacryloyl caprolactate and alkyl alpha-cyanoacryloyl butrylactate.

The alkyl ester α-cyanoacrylate monomers may be prepared through the Knoevenagel reaction of an alkyl cyanoacetate, or an alkyl ester cyanoacetate, with paraformaldehyde as disclosed in U.S. Pat. No. 3,995,641. This leads to a cyanoacrylate oligomer. Subsequent thermal cracking of the oligomer results in the formation of a α-cyanoacrylate monomer. After further distillation, an α-cyanoacrylate monomer with high purity (greater than 95.0%, preferably greater than 99.0%, and more preferably greater than 99.8%) may be obtained. Monomers prepared with low moisture content and essentially free of impurities (e.g., surgical grade) are preferred for biomedical use.

An alternative or additional α-cyanoacrylate which may be used in the adhesive/sealant compositions includes alkyl ether cyanoacrylate. Alkyl ethyl cyanoacrylates have the general formula:

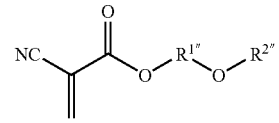

wherein R$^{1'''}$ is a straight, branched or cyclic alkyl, and R$^{2''}$ is a straight, branched or cyclic alkyl group. Preferably, R$^{1'''}$ is a C$_1$, C$_2$ or C$_3$ alkyl group, such as methyl or ethyl; and R$^{2''}$ is a C$_1$-C$_{16}$ alkyl group, more preferably a C$_1$-C$_{10}$ alkyl group, such as methyl, ethyl, propyl, isopropyl, butyl, isobutyl, pentyl, hexyl, heptyl, octyl, nonylor decyl, and even more preferably a C$_2$, C$_3$ or C$_4$ alkyl group.

Examples of alkyl ether cyanoacrylates include, but are not limited to, isopropyoxy ethyl cyanoacrylate (IPECA) and methoxy butyl cyanoacrylate (MBCA) or combinations thereof. IPECA may be represented by the formula above, wherein R$^{1'''}$ is ethylene and R$^{2''}$ is isopropyl. MBCA may be represented by the formula above, wherein R$^{1'''}$ is n-butylene and R$^{2''}$ is methyl.

Alkyl ester cyanoacrylates and alkyl ether cyanoacrylates are particularly useful for medical applications because of their absorbability by living tissue and associated fluids. It is desirable that 100% of the polymerized and applied cyanoacrylate adhesive be absorbed in a period of less than 3 years, preferably approximately 1-24 months, more preferably 1-18 months, and most preferably 3-12 months after application of the adhesive to living tissue. The absorption time may vary depending on the particular uses and tissues involved. It may be desirable for the absorption time to be longer for some types of tissue and to be shorter for other tissue types. For example, a longer absorption time may be desired when the adhesive composition is applied to hard tissues, such as bone, but a shorter absorption time may be desired when the adhesive composition is applied to softer tissues.

The selection of monomer will affect the absorption rate of the resultant polymer, as well as the polymerization rate of the monomer. Thus, two or more different monomers having varied absorption and/or polymerization rates may be used in combination to give a greater degree of control over the absorption rate of the resultant polymer, as well as the polymerization rate of the monomer. The adhesive composition may comprise a mixture of monomer species with varying absorption rates. Where two monomer species having different absorption rates are used, it is preferred that the absorption rates be sufficiently different that a mixture of the two monomers can yield a third absorption rate that is effectively different from the absorption rates of the two monomers individually. Compositions according to these embodiments are described, for example, in U.S. Patent Publication No. 2002/0037310 and U.S. Pat. No. 6,620,846, both incorporated herein by reference in their entireties.

Suitable monomer compositions may be prepared by mixing suitable quantities of an alkyl α-cyanoacrylate such as 2-octyl α-cyanoacrylate with one of butyl lactoyl cyanoacrylate (BLCA), butyl glycoloyl cyanoacrylate (BGCA), isopropyl glycoloyl cyanoacrylate (IPGCA), ethyl lactoyl cyanoacrylate (ELCA), and ethyl glycoloyl cyanoacrylate (EGCA). Such mixtures may range from ratios of about 90:10 to about 10:90 by weight, preferably about 75:25 to about 25:75 by weight.

The stability of α-cyanoacrylate monomer compositions may be adversely affected by the use of certain amounts of BLMA polymer as an absorbable viscosity modifying agent. More particularly, in general, the higher the concentration of BLMA polymer in an α-cyanoacrylate monomer composition, the less stable the monomer composition may become. To overcome the stability issue, a stabilizer or stabilizing agent may be added to the composition to prevent premature polymerization or to increase the shelf life of the α-cyanoacrylate monomeric composition. For example, boron trifluoride may be used as a stabilizing agent. Other suitable free radical stabilizing agents for use in monomeric α-cyanoacrylate adhesive compositions include, but are not limited to, hydroquinone, hydroquinone monomethyl ether, catechol, pyrogallol, benzoquinone, 2-hydroxybenzoquinone, p-methoxy phenol, t-butyl catechol, butylated hydroxy anisole, butylated hydroxy toluene, and t-butyl hydroquinone and mixtures or combinations thereof. The free radical stabilizing agents may be used in amounts from about 5 to about 10,000 ppm. In exemplary embodiments, if hydroquinone is used, the amount may be from about 5 to about 70 ppm and may be used in conjunction with butylated hydroxy anisole in an amount of about 500 to about 10,000 ppm.

The α-cyanoacrylate adhesive compositions may also optionally include at least one anionic vapor phase stabilizer and at least one anionic liquid phase stabilizer. Examples of such anionic agents are described for example, in U.S. Pat. No. 6,620,846, incorporated herein by reference in its entirety.

The anionic vapor phase stabilizers may be selected from among known stabilizers, including, but not limited to, sulfur dioxide or hydrogen fluoride. Typically, each anionic vapor phase stabilizer is added in such an amount to give a concentration of less than about 200 parts per million (ppm). In exemplary embodiments, each anionic vapor phase stabilizer is present in an amount from about 1 to about 200 ppm, preferably from about 10 to about 75 ppm, even more preferably from about 10 to about 50 ppm, and most preferably from about 10 to about 20 ppm.

The liquid phase anionic stabilizer is a very strong acid that has an aqueous $pK_a$ of less than 1.0. Examples of such very strong acids include, but are not limited to, sulfuric acid ($pK_a$ -3.0), perchloric acid ($pK_a$ -5), hydrochloric acid ($pK_a$ -7.0), hydrobromic acid ($pK_a$ -9), fluorosulfonic acid ($pKa$ <-10), and chlorosulfonic acid ($pK_a$ -10). In embodiments, the very strong acid liquid phase anionic stabilizer is added in an amount to give a final concentration of about 1 to about 200 ppm. The very strong acid liquid phase anionic stabilizer may be present in a concentration of from about 5 to about 80 ppm, preferably from about 10 to about 40 ppm. For example, the very strong acid liquid phase anionic stabilizer may be sulfuric acid or chlorosulfonic acid.

The adhesive composition may optionally include at least one secondary anionic active agent. The secondary anionic active agents may be included in the adhesive compositions to more precisely control the cure speed and stability of the adhesive as well as the molecular weight of the cured adhesive. The secondary anionic active agent would typically be an acid with a higher $pK_a$ ranging from 2 to 8, preferably from 2 to 6, and most preferably from 2 to 5. Examples of such suitable secondary anionic active agents include, but are not limited to, phosphoric acid ($pK_a$ 2.2), organic acids, such as acetic acid ($pK_a$ 4.8), benzoic acid ($pK_a$ 4.2), chloroacetic acid ($pK_a$ 2.9), cyanoacetic acid, and mixtures thereof. For example, an amount of acetic acid and/or benzoic acid may be about 25 to about 500 ppm. For acetic acid, the concentration may typically be about 50 to about 400 ppm, preferably about 75 to about 300 ppm, and more preferably about 100 to about 200 ppm.

Any mixture of stabilizers and/or secondary anionic active agents may be included in the adhesive composition as long as the mixture does not significantly inhibit the desired polymerization rate of the composition. It is generally desirable for the polymerization rate of a composition to be in a range of about thirty seconds to about five minutes. Therefore, a mixture of stabilizers and/or secondary anionic active agents that inhibit polymerization such that the polymerization rate is outside of the preferred rate window may be undesirable. Furthermore, the mixture should not, in medical adhesive compositions, show unacceptable levels of toxicity. One of ordinary skill in the art will know the levels of toxicity that are acceptable for medical uses. Thus, the amount of stabilizers and/or anionic active agents to be used can be determined by one of ordinary skill in the art without undue experimentation.

The stabilizers and secondary anionic active agents are chosen such that they are compatible with the chosen adhesive composition including the α-cyanoacrylate monomers, the BLMA polymer, boron trifluoride and other stabilizers, as well as with the packaging material and the equipment used to make and package the composition. Hence, a suitable combination should be a viscous, stabilized and substantially unpolymerized adhesive composition after packaging and sterilization.

The addition of these stabilizing agents to the α-cyanoacrylate monomer compositions may affect cure or polymerization rate of the compositions. To overcome the slow polymerization, a compatible agent which promotes initiation or acceleration of polymerization of an alkyl α-cyanoacrylate monomer or a mixture of α-cyanoacrylate monomers may be used with the monomer composition. For some medical applications, initiators or rate modifying agents providing a faster cure rate while maintaining the absorbability of the monomer composition are preferred.

In embodiments, the α-cyanoacrylate monomer composition may be stimulated to cure by a suitable quaternary ammonium salt or quaternary ammonium ether salt in as short a time as a few seconds to a few minutes. The cure rate may be closely controlled by the selection of an amount or concentration of quaternary ammonium salt to be added to the composition and may thus be readily controlled by one skilled in the art in light of the present disclosure. A suitable quaternary ammonium salt or quaternary ammonium ether salt provides consistent, controllable, and complete polymerization of the monomer or monomers so that the polymerization of the monomer or monomers can be made to occur in the time desired for the particular application.

The quaternary ammonium salt or quaternary ammonium ether salt may be any of a group of ammonium salts in which organic radicals have been substituted for all four hydrogens of the original ammonium cation. In embodiments, the quaternary ammonium salt may have the general formula A:

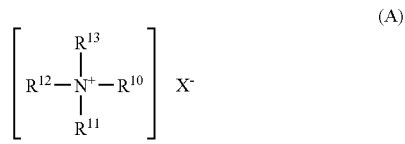

wherein $R^{10}$, $R^{11}$, $R^{12}$ and $R^{13}$ are each, independently, a substituted or unsubstituted straight, branched or cyclic alkyl group; a substituted or unsubstituted aromatic ring; or a substituted or unsubstituted aralkyl group, wherein the alkyl groups, aromatic rings or aralkyl groups may optionally further contain heteroatoms such as O, N, and S; and X is an anion such as a halide, for example chloride, bromide, or fluoride, or hydroxyl. In embodiments, $R^{10}$, $R^{11}$, $R^{12}$ and $R^{13}$ are $C_1$-$C_8$ alkyl groups, preferably, $C_1$-$C_4$ alkyl groups, or an aralkyl group. By way of example, quaternary ammonium salts may include, but are not limited to, tetrabutylammonium fluoride, tetramethylammonium fluoride, tetraethylammonium fluoride, tetraoctylammonium fluoride, benzyltrimethyl ammonium fluoride, domiphen bromide, butyrylcholine chloride, benzalkonium bromide, acetyl choline chloride, or a combination thereof.

The amount of quaternary ammonium salt added to the polymerizable monomeric α-cyanoacrylate adhesive compositions typically may depend on the α-cyanoacrylate monomers, the absorbable viscosity modifying agent, the stabilizers and the desired rate of polymerization. Typically, the quaternary ammonium salt will be present in an amount of from about 10 ppm to about 10,000 ppm, preferably about 500 ppm to about 6000 ppm.

For example, the quaternary ammonium ether salts have the general formula B:

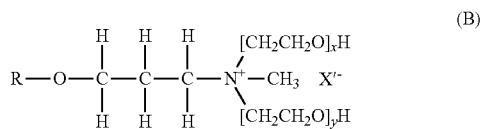

where R is a straight or branched alkyl group of from about 2 to about 20 carbon atoms, preferably from about 4 to about 16 carbon atoms; x and y represent the number of repeating units and independently are integers of from 1 to about 10, preferably from 1 to about 3, 4, or 5; and X' is a counterion selected from, for example, halides such as chloride, bromide, iodide, and fluoride, sulfate, hydrogen sulfate, sulfite, hydrogen sulfite, bisulfate, bisulfite, hydroxide, and the like.

For example, quaternary ammonium ether salts may include octadecyl poly(15)oxyethylene methyl ammonium chloride (Q-18-15), 50% active octadecyl dihydroxyethyl methyl ammonium chloride (Q-18-2(50)), or other Q-Series quaternaries available from Tomah³ Products Inc. The Tomah³ quaternaries are based on the reaction of high molecular weight aliphatic tertiary amines with an alkylating agent such as methyl chloride in a diluent such as isopropyl alcohol. Preparation of such quaternary amines is known in the art.

Suitable examples of ether amine quaternaries of formula (B) include, but are not limited to, the products Q-14-2 and Q-14-2 PG (isodecyloxypropyl dihydroxyethylmethyl ammonium chloride, where R is branched $C_{10}H_{21}$, X' is chloride and x and y yield a molecular weight of about 370), Q-17-2 and Q-17-2 PG (isotridecyloxypropyl dihydroxyethylmethyl ammonium chloride, where R is branched $C_{13}H_{27}$, X' is chloride and x and y yield a molecular weight of about 410), and Q-17-5 (isotridecyloxypropyl poly(5) oxyethylene methyl ammonium chloride, where R is branched $C_{13}H_{27}$, X' is chloride and x and y yield a molecular weight of about 535).

The amount of polymerizable quaternary ammonium ether salt added to the polymerizable monomeric α-cyanoacrylate adhesive compositions typically may depend on the polymerizable α-cyanoacrylate monomers, the viscosity modifying agent, the stabilizers and the desired rate of polymerization. Typically, the quaternary ammonium ether salt will be present in an amount of from about 0.001% to about 30%, and preferably about 0.05% to about 30%, by weight.

Other initiator or rate modifying agents may be used in combination with the quaternary ammonium fluoride or quaternary ammonium ether salt. Suitable additional initiators are known in the art and are described, for example, in U.S. Pat. Nos. 5,928,611, 6,620,846, and U.S. Patent Publication No. 2002/0037310, all incorporated herein by reference in its entirety.

In exemplary embodiments, quaternary ammonium chloride and bromide salts as polymerization initiators are preferred. By way of example, quaternary ammonium salts such as domiphen bromide, butyrylcholine chloride, benzalkonium bromide, acetyl choline chloride, among others, may be used. When the benzalkonium halide is used, it may be benzalkonium halide in its unpurified state, which comprises a mixture of varying chain-length compounds, or it may be any suitable purified compound including those having a chain length of from about 12 to about 18 carbon atoms, including but not limited to $C_{12}$, $C_{13}$, $C_{14}$, $C_{15}$, $C_{16}$, $C_{17}$, and $C_{18}$ compounds.

Other initiators or rate modifying agents may also be selected by one of ordinary skill in the art without undue experimentation. Such suitable initiators or rate modifying agents may include, but are not limited to, detergent compositions; surfactants: e.g., nonionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl)ammonium hydroxide, inner salt; amines, imines and amides, such as imidazole, arginine and povidine; phosphines, phosphites and phosphonium salts, such as triphenylphosphine and triethyl phosphite; alcohols such as ethylene glycol, methyl gallate; tannins; inorganic bases and salts, such as sodium bisulfite, calcium sulfate and sodium silicate; sulfur compounds such as thiourea and polysulfides; polymeric cyclic ethers such as monensin, nonactin, crown ethers, calixarenes and polymeric-epoxides; cyclic and acyclic carbonates, such as diethyl carbonate; phase transfer catalysts such as Aliquat 336; organometallics such as cobalt naphthenate and manganese acetylacetonate; radical initiators or accelerators, such as di-t-butyl peroxide and azobisisobutyronitrile; and a catalytic amount of an amine activated free radical initiator, accelerator, or rate modifier.

Mixtures of two or more initiators or rate modifying agents may be used with at least one quaternary ammonium fluoride salt and/or at least one quaternary ammonium ether salt. A combination of multiple initiators or rate modifying agents may be beneficial in order to tailor the initiator of the polymerizable monomer species. For example, when a mixture of monomers is used, a mixture of initiators may provide superior results in comparison to a single initiator. Also a mixture of initiators may provide one initiator that preferentially initiates one monomer, and a second initiator that preferentially initiates the other monomer, or may provide initiation rates to help ensure that both monomer species are initiated at equivalent, or desired non-equivalent, rates. In this manner, a mixture of initiators may advantageously minimize the amount of initiator to be used. Furthermore, a mixture of initiators may advantageously enhance the polymerization reaction kinetics.

The initiator or rate modifying agent may be in the form of a solid, such as a powder or a solid film, or in the form of a liquid, such as a viscous or paste-like material. The initiator or rate modifying agent may also include a variety of additives, such as surfactants or emulsifiers. Preferably, the initiator or accelerator is soluble in the monomer composition, and/or comprises or is accompanied by at least one surfactant which, in embodiments, helps the initiator or accelerator co-elute with the monomer composition. In embodiments, the surfactant may help disperse the initiator or accelerator in the monomer composition.

The initiator or rate modifying agent may be applied to the tissue or surface being treated before the monomer composition, or may be applied directly to the monomer composition when the composition is applied to the tissue. The initiator or rate modifying agent, when present, may be combined with the monomer composition just prior to applying the composition to tissue.

The selection of an initiator or rate modifying agent, when used, may additionally affect the rate at which the polymerized monomer is absorbed by living tissue. Therefore, for some medical applications, the most suitable initiators or rate modifying agents are those that initiate or accelerate polymerization of the monomer at a rate suitable for medical applications while providing a polymer that is substantially absorbed in less than three years. For purposes herein, the phrase "suitable for medical application(s)" means that the polymerization of the monomer occurs in less than 5 minutes or less than 3 minutes, preferably in less than 2.5 minutes, more preferably in less than 1 minute, and often in less than 45 seconds. The desired polymerization time may vary for different compositions and/or applications.

Other optional components may be present in the polymerizable α-cyanoacrylate compositions including, but not limited to, preservatives, heat dissipating agents, plasticizers, thixotropic agents, and colorants, which are described herein. Typically, these components will be used in amounts of up to about 25 weight %, more preferably up to about 10 weight %, and most preferably, up to about 5 weight %, based on a total weight of the composition.

The preservative may be selected from among preservatives including, but not limited to, parabens and cresols. For example, suitable parabens include, but are not limited to, alkyl parabens and salts thereof, such as methylparaben, methylparaben sodium, ethylparaben, propylparaben, propylparaben sodium, butylparaben, and the like. Suitable cresols include, but are not limited to, cresol, chlorocresol, and the like. The preservative may also be selected from other known agents including, but not limited to, hydroquinone, pyrocatechol, resorcinol, 4-n-hexyl resorcinol, captan (i.e., 3a,4,7, 7a-tetrahydro-2-((trichloromethyl)thio)-1H-isoindole-1,3 (2H)-dione), benzoic acid, benzyl alcohol, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercuric compounds such as phenylmercuric borate, phenylmercuric nitrate and phenylmercuric acetate, formaldehyde, and formaldehyde generators such as the preservatives Germall II® and Germall 115® (imidazolidinyl urea, available from Sutton Laboratories, Charthan, N.J.). Other suitable preservatives are disclosed in U.S. Pat. No. 6,579,469, the entire disclosure of which is hereby incorporated by reference. In embodiments, mixtures of two or more preservatives may also be used.

The heat dissipating agent may include liquids or solids that may be soluble or insoluble in the monomer. The liquids may be volatile and may evaporate during polymerization, thereby releasing heat from the composition. Suitable heat dissipating agents may be found in U.S. Pat. No. 6,010,714, the entire disclosure of which is incorporated herein.

The plasticizing agent imparts flexibility to the polymer that is formed from the monomer. The plasticizing agent preferably contains little or no moisture and should not significantly affect the stability or polymerization of the monomer. Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, dibutyl sebacate, diethyl sebacate, dioctyl adipate, isopropyl myristate, butyl stearate, lauric acid, trioctyl trimellitate, dioctyl glutarate, polydimethylsiloxane, and mixtures thereof. Preferred plasticizers include tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

Suitable thixotropic agents may include, but are not limited to, silica gels such as those treated with a silyl isocyanate. Examples of suitable thixotropic agents are disclosed in, for example, U.S. Pat. No. 4,720,513, the disclosure of which is hereby incorporated in its entirety.

The composition may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

Compositions of the present invention are believed to have little to no toxicity. Nevertheless, medical compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds include sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a α-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom. Other examples of formaldehyde level reducing compounds and compositions are disclosed in U.S. Pat. Nos. 6,010,714; 5,624,669; 5,582,834; and 5,575,997, the entire disclosures of which are hereby incorporated by reference.

To improve the cohesive strength of adhesives formed from the compositions of this invention, difunctional monomeric cross-linking agents may be added to the monomer compositions of this invention. Such crosslinking agents are known. Exemplary crosslinking agents are disclosed in U.S. Pat. No. 3,940,362, which is hereby incorporated by reference in its entirety. Examples of suitable crosslinking agents include, but are not limited to, alkyl bis(2-cyanoacrylates), triallyl isocyanurates, alkylene diacrylates, alkylene dimethacrylates, trimethylol propane triacrylate, and alkyl bis(2-cyanoacrylates).

To improve the adhesion between substrates (e.g. tissue surface) and the compositions of this invention, priming agents may be used to condition the substrate prior to applying in the α-cyanoacrylate monomers. Suitable primers include, but are not limited to, ph-modifying agents (e.g. organic or inorganic bases), ionic and non-ionic surfactants, and organic or inorganic salts. Other suitable priming agents can be readily identified by one skilled in the art in light of the present disclosure.

The compositions of this invention may further contain fibrous reinforcements and colorants such as dyes, pigments, and pigment dyes. Examples of suitable fibrous reinforcements include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2-naphthalene-sulfonic acid (FD+C Yellow No. 6); 9-(o-carboxyphen0yl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper.

The composition may also optionally include at least one biological or therapeutic agent. The variety of biological/therapeutic agents that can be used in conjunction with the adhesive composition of the invention is vast. In general, biological/therapeutic agents which may be administered with adhesive/sealant compositions of the invention include, but are not limited to, anti-infective agents, such as antibiotics, antimicrobial agents (e.g. Diiodomethyl-p-tolylsulfone, 2,4,4'-Trichloro-2'-Hydroxydiphenyl Ether or combination thereof), antiseptics, bacteriocins, bacteriostats, disinfectants, fungicides, antibacterial, and antiviral agents; analgesics and analgesic combinations; anti-inflammatory agents; naturally derived or genetically engineered proteins, polysaccharides, glycoproteins, or lipoproteins; oligonucleotides, antibodies, antigens, cholinergics, cystostatics heparin neutralizers, procoagulants and hemostatic agents, such as prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents and synthetic peptides having hemostatic activity.

The composition may be used in surgical procedures as an adjunct to primary wound closure devices, such as staples, sutures, tapes, meshes to seal potential leaks of gasses, liquids, or solids. The surgical adhesive/sealant may be applied to tissue as a part of a surgical procedure in various forms, for example: liquid, powder, film, sponge or foam, impregnated fabric, impregnated sponge or foam, and spray. The instant adhesive compositions are particularly advantageous in a surgical context because of their absorbable nature.

The composition may be applied in single or multiple applications. For example, the adhesive compositions may be applied in a first layer, and after the first layer is allowed to fully or partially polymerize, a subsequent layer may be added. Such a process may be conducted numerous times, depending on the size of the wound and the amount of adhesive applied in each application.

The monomer composition may be packaged in any type of suitable container fabricated from materials including, but not limited to, glass, plastic, metal packages, and film-formed packages. Suitable containers preferably include those into which the compositions may be dispensed and sterilized without unacceptable damage to, or degradation of, the container or the components of the monomer composition. As disclosed in U.S. Patent Publication No. 2003/0039781, the entire disclosure of which is hereby incorporated by reference, post-halogenated (e.g., fluourinated) or silanized polymeric barrier layers on at least the monomer-contacting surfaces of the container provide a superior shelf-life for monomer compositions. Glass is especially preferred when sterilization is achieved with dry heat because of the lack of stability of many plastics at temperatures used for dry heat sterilization (typically at least about 140° C.). Examples of types of containers include, but are not limited to, ampoules, vials, syringes, pipettes, and the like.

The present invention also includes a saleable kit for delivering an absorbable α-cyanoacrylate adhesive to tissue. The kit comprises a saleable package comprising a first container that contains at least one α-cyanoacrylate monomer; and a polymerization initiator or rate modifying agent. The kit may comprise a second container containing the initiator or accelerator. Alternatively, the first container may have the initiator or accelerator in or on it as long as the initiator or accelerator is not in contact with the monomer prior to the desired use. The initiator or accelerator is selected so that it functions in conjunction with the co-packaged polymerizable monomer composition to initiate polymerization of the monomer or modify (e.g., accelerate) the rate of polymerization of the monomer to form a polymeric adhesive. The proper combination of initiator or accelerator and polymerizable monomer can be determined by one of skill in the art without undue experimentation in light of the present disclosure. The kit may also include a brush, swab, or sponge to assist in applying the composition to living tissue. The kit is also preferably sterilized; however, the containers and components may be sterilized separately or together. Preferably, kits and the kit components (including compositions) of the present invention have a sterility level in the range of $10^{-3}$ to $10^{-6}$ Sterility Assurance Level (SAL) and are sterile for surgical purposes. Various designs of such kits are disclosed, for example, in U.S. Pat. No. 6,802,416, the entire disclosure of which is incorporated by reference herein. The sterilization may be accomplished by techniques known to the skilled artisan, and is preferably accomplished by methods including, but not limited to, chemical, physical, and irradiation methods.

Examples of physical methods include, but are not limited to, sterile fill, filtration, sterilization by heat (dry or moist), and retort canning. Examples of irradiation methods include, but are not limited to, gamma irradiation, electron beam irradiation, and microwave irradiation.

The compositions described herein have multiple medical applications. For example, as an internal surgical adhesive and sealant, the adhesive can bond tissue to tissue, tissue to medical device (e.g. meshes, clips and films), and medical device to medical device. As a sealant, the composition can be coated on a tissue, on a medical device, or on the interface between a medical device and tissue to prevent leaks. The composition can be used to form films in situ that may have applications such as for the prevention of surgical adhesions. The composition can be used to form foams in situ that may have applications such as a filler (e.g. dead space removal, reconstructive, and cosmetic surgeries), bulking agents, tissue engineering (e.g. scaffolds) materials, and others where foams and sponges are useful. The composition can be formulated so that it is injectable and used to form gels in situ that are localized, and adherent to tissue, thus staying at the site where they are injected. The injectable formulation may have applications such as a delivery matrix for cells and other biologicals, bioactive agents and pharmaceutical or neutraceutical agents, as embolization agents, and as means to localize contrasting agents.

As a filler, the monomer composition may be used as a facial, defect or void filler. For example, the composition may be applied in the interstices of an internal void and allowed to polymerize therein, such that the resultant polymer fills the internal cavities and voids, penetrating and conforming to the interstices and pores of the tissue. Thus, the composition may be used after a broad number of procedures having potential risk of dead space formation, including, but not limited to, radical mastectomy (i.e. breast and regional lymph nodes removal for cancer treatment), breast reconstruction and augmentation procedure, reconstructive or cosmetic abdominoplasty and liposuction, face-lift, cesarean section and hysterectomy in obese patients, orthopedic procedures on thigh region, incisional hernia repair, lipoma excision, and traumatic lesions, i.e. closed trauma.

EXAMPLES

The present invention will be further understood by reference to the following non-limiting examples.

Example 1A

Synthesis of a Butyl Lactoyl Methacrylate (BLMA) Monomer

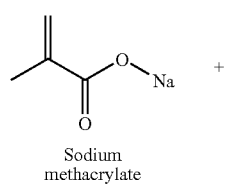

Sodium methacrylate

+

Butyl 2-bromo propionate (BBP)

→ DMF / HQ

Butyl latoyl methacrylate

A 3-neck, round bottom flask was charged with butyl 2-bromo propionate (BBP), sodium methacrylate, hydroquanione and DMF in the ratio of 1.00, 1.25, 0.0185, and 9.00. The flask was fitted with an overhead stirrer, condenser, thermocouple, and heating mantle. The overhead stirrer was set to about 300 rpm and the J-chem was set to 90° C. The reaction mixture was held at 90° C. for 1.5 hours and then allowed to cool to room temperature. Once the reaction mixture cooled to room temperature, toluene was added to cause precipitation of any dissolved sodium bromide. The entire mixture was then filtered through a glass frit, and the salt was washed with additional toluene. Once all the precipitated salt was removed, the reaction mixture was washed three times with deionized water to remove any residual salt and the DMF. The material was then dried, concentrated, and purified by vacuum distillation.

Example 1B

Synthesis of the BLMA Polymer

A 3-neck, round bottom flask was charged with BLMA monomer. The flask was fitted with an overhead stirrer, $N_2$ sparging tube, thermocouple, and heating mantle. The monomer was bubbled with nitrogen for a minimum of 30 minutes. The $N_2$ sparging tube was removed and the flask was kept under a nitrogen blanket. The overhead stirrer was set to about 400 rpm and then a first dose of VAZO™ 67 free radical initiator was added (0.015% by weight compared to the monomer). The flask was heated to 65° C. and vigorously stirred for about 1.5 hours. A second dose of VAZO™ 67 free radical initiator was then added to thicken the reaction mixture by 0.03% by weight compared to the monomer. The mixture was stirred for additional 15 minutes.

After the second dose of VAZO™ 67, the reaction mixture became exothermic and extremely viscous. Once the mixture became exothermic, it was transferred into a Teflon coated pan and placed in a vacuum oven at 90° C. overnight. The vacuum oven was kept under vacuum, but slightly vented, to remove any residual monomer. The polymer was further purified by precipitating with methanol.

The polymer synthesis was monitored by Gel Permeation Chromatography (GPC), using a conventional calibration curve created with polymethylmethacrylate standards. A total of six bulk polymerization experiments were conducted. The results of the experiments are shown in Table 1. The molecular weight, Mw, for each of the samples was over 500,000. It is preferred that the molecular weight be greater than 300,000 and more preferred that the molecular weight be greater than 500,000; therefore, each of the samples exhibited a desirable molecular weight. The polydispersity index, Mw/Mn, for each sample was less than 3.0. It is preferred that the polydispersity index be less than 3.5 and more preferred that it be less than 3.0; therefore, each of the samples exhibited a desirable polydispersity index. In addition, the relative similarity of the results for each of the samples indicates favorable reproducibility of the BLMA polymer using the described synthesis process. Such reproducibility indicates that the described synthesis process should be commercially viable.

TABLE 1

| Sample | Mn | Mw | Mw/Mn |
|---|---|---|---|
| 1 | 641,696 | 1,442,000 | 2.247 |
| 2 | 357,932 | 744,930 | 2.081 |
| 3 | 497,069 | 967,260 | 1.946 |
| 4 | 456,713 | 1,224,000 | 2.681 |
| 5 | 536,795 | 1,037,000 | 1.931 |
| 6 | 515,528 | 953,920 | 1.850 |

Example 2

Effect of BLMA Polymer on Viscosity and Stability of a Monomeric α-Cyanoacrylate Formulation To evaluate the effect of the use of BLMA polymer as a viscosity modifying agent on the viscosity of a α-cyanoacrylate adhesive formulation, monomeric α-cyanoacrylate compositions with 0%, 5% and 7.5% by weight of BLMA polymer were prepared and measured for viscosity at various time points at 80° C. The BLMA polymer had a molecular weight of about 1.2 million Daltons and was precipitated with methanol. The monomeric α-cyanoacrylate composition included 2-octylcyanoacrylate, less than about 70 ppm hydroquinone, about 1600 ppm butylated hydroxyanisole, about 110 ppm p-methoxyphenol, about 20 ppm sulfuric acid, about 106 ppm acetic acid, and about 15 ppm sulfur dioxide. In one formulation, about 80 ppm boron trifluoride was added to the monomeric α-cyanoacrylate composition with 5 wt % BLMA polymer. The formulations were aliquoted into glass ampoules and sterilized at 159° C. for 35 minutes.

The viscosity was measured using a Brookfield Viscometer with spindle CP-40 by known methods at 0, 6, 12, 18 and 24 days. At 0 and 6 days, the formulations with the BLMA polymer had higher viscosity than the formulation without the BLMA polymer. As shown in Table 2, the viscosity of the formulation with 7.5 wt % BLMA polymer had more than 2-fold increase over the formulations with 5 wt % BLMA polymer. Also the viscosity of the formulation with 5 wt % BLMA polymer and $BF_3$ was similar to the viscosity of the formulation with 5 wt % BLMA polymer. At 12 days, the viscosity levels for the formulations with 5 wt % BLMA polymer increased slightly, and the viscosity level for the formulation with 7.5 wt % BLMA polymer experienced approximately a 1.7-fold increase. At 18 and 24 days, the viscosity levels of the three formulations without $BF_3$ increased significantly. The viscosity of the formulation with $BF_3$ increased slightly to 347 cps at 18 days and to 386 cps at 24 days. These results indicated that the addition of BLMA polymer increased the viscosity but decreased the stability of the monomeric α-cyanoacrylate formulation, and the addition of $BF_3$ maintained the stability of the viscous monomeric α-cyanoacrylate formulation.

TABLE 2

| Formulation Description | Viscosities (cps) | | | | | |
|---|---|---|---|---|---|---|
| | Pre Dry Heat | Post Dry Heat | 6 Days @ 80 C. | 12 Days @ 80 C. | 18 Days @ 80 C. | 24 days @ 80 C. |
| 5% p-BLMA | 251 | 248 | 250 | 334 | 588 | 1813 |
| 5% p-BLMA w/ 80 ppm BF3 | 269 | 273 | 273 | 316 | 347 | 386 |
| 7.5% p-BLMA | 708 | 696 | 721 | 1200 | 2476 | N/A |
| Control, no polymer | 6 | 6 | 6.4 | 8.4 | 31.8 | 810 |

To further evaluate the effect of BLMA polymer and BF$_3$ on stability and reactivity, formulations of monomeric α-cyanoacrylate compositions with 5% and 7.5% by weight of BLMA polymer; and with 0 ppm and 80 ppm of BF$_3$, respectively, were prepared and measured for viscosity at various time points at 80° C. Precipitated and non-precipitated BLMA polymers with an average molecular weight of about 1.3 million Daltons were used. The formulations were aliquoted into glass ampoules and sterilized using dry heat. The formulations were measured for stability and reactivity.

The stability was measured by viscosity as described above. As shown in Table 3, the viscosity levels of the formulations with 7.5 wt % BLMA polymer increased to a higher amount than those of the formulation with 5 wt % BLMA polymer. Also, the viscosity of the formulations with precipitated BLMA polymers, in both 5% and 7.5% by weight, had a less increased amount compared to those of the formulations with non-precipitated BLMA polymer. For all samples with 80 ppm BF$_3$, the viscosity levels increased slightly, from 174 to 205 cps for 5 wt % precipitated BLMA polymer, from approximately 200 to 260 cps for 5 wt % non-precipitated BLMA polymer, from approximately 460 to 529 cps for 7.5 wt % precipitated BLMA polymer, and from approximately 550 to 676 cps for 7.5 wt % non-precipitated BLMA polymer. These results indicated that without BF$_3$ the monomeric formulation with 5 wt % precipitated BLMA polymer was more stable. Also, the results indicated that the addition of BF$_3$ increased the stability of the viscous α-cyanoacrylate monomeric formulations.

TABLE 3

| | | | | Viscosities (cps) | | | | |
|---|---|---|---|---|---|---|---|---|
| | Formulation Description | | | Pre | Post | | 12 | 15 |
| ID | p-BLMA wt % | Polymer Description | [BF3] ug/g | Dry Heat | Dry Heat | 6 Days @ 80 C. | Days @ 80 C. | Days @ 80 C. |
| A1 | 5% | 1 × precip. | 0 | 178 | 178 | 196 | 271 | 297 |
| B1 | 5% | No precip. | 0 | 201 | 197 | 220 | 338 | 465 |
| C1 | 5% | 1 × precip. | 80 | 174 | 174 | 186 | 192 | 206 |
| D1 | 5% | No precip. | 80 | 201 | 206 | 218 | 236 | 260 |
| A2 | 7.5% | 1 × precip. | 0 | 466 | 491 | 531 | 678 | 938 |
| B2 | 7.5% | No precip. | 0 | 524 | 530 | 617 | 1047 | 1680 |
| C2 | 7.5% | 1 × precip. | 80 | 448 | 462 | 479 | 505 | 529 |
| D2 | 7.5% | No precip. | 80 | 535 | 550 | 589 | 646 | 676 |

The reactivity of the samples was measured by a gel time study. A constant amount of a benzyltrialkyl chloride (BTAC) polymerization initiator (0.225%) was added to all formulations for a gel time study. The gel time study was conducted with the method as stated. The amount of 1.850 g±0.050 g of the α-cyanoacrylate formulation was added to a 7 mL glass scintillation vial with stir bar. The vial was placed on a stir plate and the speed of the stirring was set such that a vortex was reached half way from the surface of the liquid to the bottom of the vial. 200 uL of the appropriate concentration of initiator solution was added into the vial. Timing was started immediately with a stop watch when the initiator solution was added. The timing was stopped when the stir bar stopped, the vial fell over, and/or the liquid reacted violently.

As shown in Table 4, the gel time for all formulations with BF$_3$ was more than 100 seconds compared to 50 seconds for the formulation without BF$_3$. These results indicated that the addition of BF$_3$ increased the stability but decreased the reactivity of the viscous monomeric α-cyanoacrylate formulation, and that BTAC is not an effective initiator or rate modifying agent for the formulations containing BF$_3$ as the stabilizing agent.

TABLE 4

| | | | | Gel Times (s) | | | |
|---|---|---|---|---|---|---|---|
| | Formulation Description | | | Post | | 12 | 18 |
| ID | p-BLMA wt % | Polymer Description | [BF3] (ug/g) | Dry Heat | 6 Days @ 80 C. | Days @ 80 C. | Days @ 80 C. |
| A1 | 5% | 1 × precip. | 0 | 47 | 46 | 21 | 11 |
| B1 | 5% | No precip. | 0 | 53 | 33 | 10 | 15 |
| C1 | 5% | 1 × precip. | 80 | 187 | 190 | 187 | 142 |
| D1 | 5% | No precip. | 80 | 204 | 205 | 155 | 107 |
| A2 | 7.5% | 1 × precip. | 0 | 39 | 42 | 23 | 23 |

TABLE 4-continued

|  | Formulation Description | | | Gel Times (s) | | | |
|---|---|---|---|---|---|---|---|
| ID | p-BLMA wt % | Polymer Description | [BF3] (ug/g) | Post Dry Heat | 6 Days @ 80 C. | 12 Days @ 80 C. | 18 Days @ 80 C. |
| B2 | 7.5% | No precip. | 0 | 51 | 26 | 17 | 24 |
| C2 | 7.5% | 1 × precip. | 80 | 200 | 183 | 187 | 311 |
| D2 | 7.5% | No precip. | 80 | 443 | 249 | 279 | 124 |
| Control | 0.0% | N/A | 0 | 45 | 24 | 5 | N/A |

Example 3

Effect of Q-18-15 on Stability and Reactivity of the Viscous α-Cyanoacrylate Formulation To address the reduced reactivity of the α-cyanoacrylate formulations with BLMA polymer and $BF_3$, the quaternary ammonium ether salt, Q-18-15, was employed as an initiator or rate modifying agent for the formulation. Results of the stability and the reactivity studies are summarized in Tables 5 and 6.

For the stability study, an α-cyanoacrylate monomeric composition as described in Example 2 with precipitated BLMA polymer in 7.5% and 8.2% by weight and 80 ppm of $BF_3$ were prepared. Two formulations with non-precipitated BLMA polymer in 7.5% and 10% by weight and 80 ppm $BF_3$ were also prepared. Formulations with precipitated BLMA polymer in 7.5% by weight, without BLMA polymer but with 80 ppm $BF_3$, and without BLMA polymer or $BF_3$ were used as control samples. The BLMA polymer, both precipitated and non-precipitated, had an average molecular weight of 1.3 million Daltons. All formulations were aliquoted into glass ampoules and sterilized through a vascular sealant dry heat sterilization cycle. The formulations were measured for stability by a viscosity study at 80° C. The results are shown in Table 5.

As observed in Example 2, the viscosity levels of the formulations with precipitated BLMA polymer were lower than those of the formulations with non-precipitated BLMA polymer. In addition, the viscosity of the formulation containing $BF_3$ increased to no more than 2-fold at 24 days. It was also observed that the viscosity of the formulations containing higher concentrations of BLMA polymer had higher levels. For example, the formulation containing 10% by weight of BLMA polymer had the highest viscosity level at approximately 1251 cps at 0 day and 2527 cps at 24 days, compared to 649 cps at 0 day and 838 cps at 24 days for the 8.2% by weight pBLMA formulation; and to 496 cps at 0 day and 634 at 24 days for the 7.5% by weight pBLMA formulation. The 7.5% by weight pBLMA formulation with the addition of $BF_3$ had slightly increased levels of viscosity, from 496 cps to 634 cps at 24 days for precipitated polymer and from 516 cps at 0 day to 912 cps at 24 days for non-precipitated polymer. However, the viscosity of 7.5% by weight formulation without $BF_3$ increased significantly over time, from 516 cps at 0 day to 2605 cps at 18 days, and to complete solidification at 21 and 24 days.

TABLE 5

| | Formulation Description | | | Viscosities (cps) | | | | | | |
|---|---|---|---|---|---|---|---|---|---|---|
| Formulation ID | Polymer wt % | Polymer Description | [BF3] (ug/g) | Pre Dry Heat | Post Dry Heat | 6 Days @ 80 C. | 12 Days @ 80 C. | 18 Days @ 80 C. | 21 Days @ 80 C. | 24 Days @ 80 C. |
| D73-61-A1 | 8.2% | 1 × precip. | 80 | 587 | 649 | 638 | 636 | 708 | 769 | 838 |
| D73-61-A2 | 7.5% | 1 × precip. | 80 | 458 | 496 | 486 | 490 | 533 | 611 | 634 |
| D73-61-B1 | 10.0% | No precip. | 80 | 1227 | 1251 | 1343 | 1530 | 1876 | 2124 | 2527 |
| D73-61-B2 | 7.5% | No precip. | 80 | 517 | 570 | 573 | 608 | 725 | 819 | 912 |
| D73-61-C1 | 0.0% | N/A | 0 | 5.8 | 6.1 | 6.8 | 11 | 124 | n/a | n/a |
| D73-61-C2 | 0.0% | N/A | 80 | 5.8 | 6.1 | 6.7 | 7 | 8 | 10 | n/a |
| D73-61-C3 | 7.5% | 1 × precip. | 0 | 480 | 516 | 605 | 902 | 2605 | n/a | n/a |

To conduct a gel time study, Q-18-15 was used as an initiator or rate modifying agent for the above formulations containing $BF_3$ and BHC was used as an initiator or rate modifying agent for the control formulations without polymer or $BF_3$. The Q-18-15 from Tomah[3] Products, Inc in acetone was used in amounts of 1.5% by weight of the monomeric composition for the control formulation with 80 ppm $BF_3$, and the formulations with 7.5% or 8.2% by weight of BLMA polymer, both with and without $BF_3$. The BHC in acetone was used in an amount of 0.225% by weight of the monomeric composition for the control formulation without polymer or $BF_3$. The formulation containing 10% by weight BLMA polymer and 80 ppm $BF_3$ was not examined as the sample was very viscous and could not be stirred as required by the gel time study method. These compositions were applied via prototype applicators in a gel time study, which was performed according to the method described above in Example 2. The results of the gel time study are in Table 6. These results show that the quaternary ammonium ether salt Q-18-15 was able to adequately promote initiation of polymerization of the viscous $BF_3$ formulations. The average gel time of the viscous $BF_3$ formulations was 68 seconds compared to 44 seconds for the control formulation without polymer or $BF_3$ and to 42 seconds for the 7.5% by weight control pBLMA formulation.

TABLE 6

| Formulation ID | Polymer wt % | Polymer Description | [BF3] (ug/g) | Post Dry Heat Gel Times (s) |
|---|---|---|---|---|
| D73-61-A1 | 8.2% | 1 × precipitated | 80 | 52 |
| D73-61-A2 | 7.5% | 1 × precipitated | 80 | 62 |
| D73-61-B1 | 10.0% | No precipitation | 80 | N/A |
| D73-61-B2 | 7.5% | No precipitation | 80 | 81 |
| D73-61-C1 | 0.0% | N/A | 0 | 44 |
| D73-61-C2 | 0.0% | N/A | 80 | 77 |
| D73-61-C3 | 7.5% | 1 × precipitated | 0 | 42 |

Example 4

Effect of BLMA Polymer on Viscosity of a Blended Monomeric α-Cyanoacrylate Formulation Two viscous monomeric α-cyanoacrylate compositions were prepared for viscosity studies. The first composition was the composition from Example 1 containing 2-octyl cyanoacrylate, and the second composition was a blended monomeric α-cyanoacrylate composition including 75%/25% 2-octyl cyanoacrylate/butyl lactoyl cyanoacrylate, less than about 70 ppm hydroquinone, about 1600 ppm butylated hydroxyanisole, about 110 ppm p-methoxyphenol, about 20 ppm sulfuric acid, about 106 ppm acetic acid, and about 15 ppm sulfur dioxide. Both compositions were mixed with 7.5% by weight of BLMA polymer and 80 ppm $BF_3$.

The α-cyanoacrylate compositions were aliquoted into glass ampoules and sterilized by dry heat. The glass ampoules were cracked using standard scoring and cracking techniques. Then a blunt needle was attached to a syringe to draw up a necessary amount of viscous composition from the cracked glass ampoule. The blunt needle was then removed from the syringe.

Separately, syringe applicator devices with Porex® plugs were assembled. An initiated tip for each syringe applicator device was prepared by solvent casting either 10% by weight of Q-18-15 or 6400 ppm of BTAC in methanol on a Porex® plug, which was then placed in the syringe applicator device near the tip of the device. The applicator devices were sterilized by e-beam at 25 kGy. The prepared syringe applicator devices were connected to the syringes containing viscous monomeric α-cyanoacrylate compositions.

Specifically, a syringe containing a viscous composition was mated in a facing arrangement to a syringe applicator device using a luer connector. The viscous formulation was mixed with initiator contained in the Porex® plug of the syringe applicator device by alternatingly pushing the plungers of the syringe and the syringe applicator device to force the viscous composition back and forth from the syringe to the syringe applicator device through the Porex® plug. After several rounds of mixing, the viscosity of the mixed composition was measured. As indicated previously, mixed composition viscosity is used as a determination of mixed composition stability.

The stability of the mixed compositions was measured by viscosity at 0, 6, 12, and 18 days at 80° C. using a Brookfield Viscometer. The results are contained in Table 7. As shown, the viscosity of the 2-octyl cyanoacrylate composition with BLMA polymer and $BF_3$ was 767 cps at 0 day and increased slightly to 893 cps at 18 days. Similarly, the viscosity of the blended α-cyanoacrylate composition with BLMA polymer was 751 cps at 0 day and was 1113 cps at 18 days.

TABLE 7

| Formulation Description | Viscosity (cps) | | | |
|---|---|---|---|---|
| | T (0 d) | T (6 d) | T (12 d) | T (18 d) |
| 2-OCA and BLCA w/ $BF_3$ and pBLMA | 751 | 807 | 877 | 1113 |
| 2-OCA w/ BF3 and pBLMA | 767 | 779 | 825 | 893 |

What is claimed is:

1. A polymerizable adhesive composition comprising at least one α-cyanoacrylate monomer and at least one absorbable viscosity modifying agent, wherein the absorbable viscosity modifying agent has repeated units of the following structure:

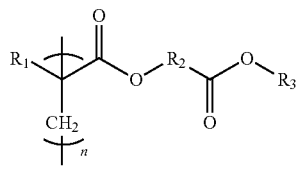

wherein $R_1$ is a methyl group or a hydrogen, $R_2$ is a straight, branched or cyclic alkyl group having from 1 to 6 carbon atoms, $R_3$ is a straight, branched or cyclic alkyl group having from 1 to 12 carbon atoms, and n is 2 or more.

2. The polymerizable adhesive composition of claim 1, wherein the at least one absorbable viscosity modifying agent is selected from the group consisting of a polymer of 2-methoxy-2-oxoethyl acrylate, 2-ethoxy-2-oxoethyl acrylate, 2-oxo-2-propoxyethyl acrylate, 2-butoxy-2oxoethyl acrylate, 2-methoxy-2-oxoethyl methacrylate, 2-ethoxy-2-oxoethyl methacrylate, 2-oxo-2-propoxyethyl methacrylate, 2-butoxy-2-oxoethyl methacrylate, 1-methoxy-1-oxopropan-2-yl acrylate, 1-ethoxy-1-oxopropan-2-yl acrylate, 1-methoxy-1-oxopropan-2-yl methacrylate, 1-ethoxy-1-oxopropan-2-yl methacrylate, 1-oxo-1-propoxypropan-2-yl methacrylate, 1-butoxy-1-oxopropan-2-yl methacrylate, and mixtures thereof.

3. The polymerizable adhesive composition of claim 1, wherein the at least one absorbable viscosity modifying agent is 1-butoxy-1-oxopropan-2-yl methacrylate polymer.

4. The polymerizable adhesive composition of claim 1, wherein the at least one α-cyanoacrylate monomer is selected from the group consisting of dodecyl cyanoacrylate, 2-ethylhexyl cyanoacrylate, methoxyethyl cyanoacrylate, 2-ethoxyethyl cyanoacrylate, octyl cyanoacrylate, butyl cyanoacrylate, ethyl cyanoacrylate, methyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, butyl lactoyl cyanoacrylate, butyl glycoloyl cyanoacrylate, isopropyl glycoloyl cyanoacrylate, ethyl lactoyl cyanoacrylate, ethyl glycoloyl cyanoacrylate, isopropoxy ethyl cyanoacrylate, methoxy butyl cyanoacrylate, or mixtures thereof.

5. The polymerizable adhesive composition of claim 1, wherein the at least one α-cyanoacrylate monomer is selected from the group consisting of octyl cyanoacrylate, butyl lactoyl cyanoacrylate, and mixtures thereof.

6. The polymerizable adhesive composition of claim 1, wherein the at least one α-cyanoacrylate monomer is selected from the group consisting of an alkyl cyanoacrylate, an alkyl ester cyanoacrylate, an alkyl ether cyanoacrylate, and mixtures thereof.

7. The polymerizable adhesive composition of claim 6, wherein the alkyl cyanoacrylate is octyl cyanoacrylate.

8. The polymerizable adhesive composition of claim 6, wherein the alkyl ester cyanoacrylate is butyl lactoyl cyanoacrylate.

9. The polymerizable adhesive composition of claim 1, further comprising at least one of a stabilizing agent, an initiator, a preservative, a plasticizer, a heat dissipating agent, a thixotropic agent, a colorant, a therapeutic agent, a colorant, a therapeutic agent, a biocompatible agent or mixtures thereof.

10. The polymerizable adhesive composition of claim 9, wherein the stabilizing agent comprises boron trifluoride.

11. The polymerizable adhesive composition of claim 9, wherein the stabilizing agent is present in an amount from about 5 to about 10,000 ppm.

12. The polymerizable adhesive composition of claim 9, wherein the initiator comprises a quaternary ammonium salt.

13. The polymerizable adhesive composition of claim 12, wherein the quaternary ammonium salt is present in an amount from about 0.005% to about 30% by weight of the composition.

14. The polymerizable adhesive composition of claim 1, wherein the absorbable viscosity modifying agent is present in an amount from about 1% to about 15% by weight of the polymerizable adhesive composition.

15. The polymerizable adhesive composition of claim 14, wherein the absorbable viscosity modifying agent is present in an amount from about 2% to about 8% by weight of the polymerizable adhesive composition.

16. The polymerizable adhesive composition of claim 1, wherein the viscosity of the composition is from about 50 centipoise to about 800 centipoise at 25° C.

17. A polymerized material comprising (a) a polymer formed from at least one α-cyanoacrylate monomer and (b) at least one absorbable viscosity modifying agent, wherein the viscosity modifying agent has repeated units of the following structure:

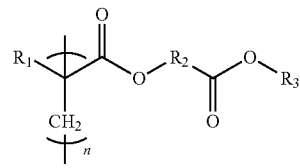

wherein $R_1$ is a methyl group or a hydrogen, $R_2$ is a straight, branched or cyclic alkyl group having from 1 to 6 carbon atoms, $R_3$ is a straight, branched or cyclic alkyl group having from 1 to 12 carbon atoms, and n is 2 or more.

18. The polymerized material of claim 17, wherein the absorbable viscosity modifying agent is 1-butoxy-1-oxopropan-2-yl methacrylate polymer.

19. A polymerized material comprising:
(a) a polymer formed from at least one α-cyanoacrylate monomer and
(b) at least one absorbable viscosity modifying agent selected from the group consisting of a polymer of 2-methoxy-2-oxoethyl acrylate, 2-ethoxy-2-oxoethyl acrylate, 2-oxo-2-propoxyethyl acrylate, 2-butoxy-2oxoethyl acrylate, 2-methoxy-2-oxoethyl methacrylate, 2-ethoxy-2-oxoethyl methacrylate, 2-oxo-2-propoxyethyl methacrylate, 2-butoxy-2-oxoethyl methacrylate, 1-ethoxy-1-oxopropan-2-yl acrylate, 1-methoxy-1-oxopropan-2-yl methacrylate, 1-ethoxy-1-oxopropan-2-yl methacrylate, 1-oxo-1-propoxypropan-2-yl methacrylate, 1-butoxy-1-oxopropan-2-yl methacrylate, and mixtures thereof and further wherein the weight average molecular weight (Mw) is at least 300 kDa.

* * * * *